United States Patent
Erath

(10) Patent No.: US 6,829,048 B2
(45) Date of Patent: Dec. 7, 2004

(54) FLAME ATOMIZATION DEVICE

(75) Inventor: Michael Erath, Uberlingen (DE)

(73) Assignee: Berthold GmbH & Co. KG (DE)

( * ) Notice: Subject to any disclaimer, the term of this patent is extended or adjusted under 35 U.S.C. 154(b) by 236 days.

(21) Appl. No.: 10/143,222

(22) Filed: May 10, 2002

(65) Prior Publication Data

US 2002/0192616 A1 Dec. 19, 2002

(30) Foreign Application Priority Data

May 11, 2001 (DE) .......................................... 101 22 873

(51) Int. Cl.[7] .............................................. G01N 21/72
(52) U.S. Cl. ...................................... 356/315; 356/417
(58) Field of Search ................................. 356/315, 417

(56) References Cited

U.S. PATENT DOCUMENTS 3,586,441 A * 6/1971 Smith et al. ................. 356/315
3,817,693 A * 6/1974 Sebens et al. ............... 431/153

FOREIGN PATENT DOCUMENTS

| DE | 72 34 447 | 2/1973 |
|---|---|---|
| DE | 75 16 802 | 11/1976 |
| DE | 30 10 350 A1 | 9/1981 |
| DE | 242 870 A1 | 11/1985 |
| DE | 35 41 107 A1 | 9/1987 |

OTHER PUBLICATIONS

William B. Barnett, Acid Interferences in Atomic Absorption Spectrometry, Analytical Chemistry, vol. 44, No. 4, Apr. 1972, pp. 695–698.

* cited by examiner

Primary Examiner—F. L. Evans
(74) Attorney, Agent, or Firm—St. Onge Steward Johnston & Reens LLC

(57) ABSTRACT

A flame atomization device, especially for an atom absorption spectrometer, is disclosed. The flame atomization device includes at least one mixer chamber and an atomizer leading into the mixer chamber, and a burner head mounted on the mixer chamber's burner connection piece. A slip casing is mounted so that it can slide between a closed position and an open position in relation to the burner connection piece while, in the open position, at least one pressure reduction outlet is opened in the burner connection piece.

25 Claims, 2 Drawing Sheets

FLAME ATOMIZATION DEVICE

This application claims priority of pending German Patent Application 101 22 873.2 filed on May 11, 2001.

FIELD OF THE INVENTION

The invention relates to a flame atomization device, especially for an atom absorption spectrometer, with at least one mixer chamber and an atomizer leading into said mixer chamber, and with a burner head mounted on the mixer chamber's burner connection piece.

Such a flame atomization device for an atom absorption spectrometer serves to bring a sample into a measurable atomic state. For this purpose, the sample is introduced by the atomizer, especially in the form of aerosol, into the mixer chamber. There, the sample is mixed with a fuel gas and conducted to the burner head via the burner connection piece. Then the fuel gas enriched with the sample combusts inside the burner head. The sample stimulated by the flame can be analyzed by the atom absorption spectrometer. In the course of regular operation, the speed with which the fuel gas enriched with the sample escapes exceeds the speed of combustion. Consequently, the corresponding flame is always found outside the mixer chamber or burner connection piece. Yet a certain kind of error, such as leaks or the use of laughing gas, may lead to flashbacks of the flame. Laughing gas for example, can lead to a very high combustion speed and is therefore difficult to handle.

During such a flashback of the flame, the flame burns inside the burner head, in the area of the burner connection piece, and possibly even in the remaining area of the mixer chamber. These areas possess comparatively large cross-sections in which the speed of the gas is low. This results in an explosion-like blow-up and a corresponding explosive excess pressure. Yet such an explosive excess pressure must not lead to the destruction of the components, and in addition, the flame atomization device should safely switch off in case such an excess pressure occurs.

With flame atomization devices currently in use, in cases of such explosive overpressure a corresponding pressure release was ensured, for instance by means of a burner head that flies off. The burner head was secured by a rope or other recovery devices. With other flame atomization devices, such a pressure relief occurred, for example, through a pretensioned pressure release valve.

Finally, there are known flame atomization devices, which use additional pressure relief devices such as removable plugs, a bursting disk, or something similar.

BACKGROUND OF THE INVENTION

The flame atomization devices known from practice have the disadvantage of requiring additional parts, and of needing comparatively great cost when they have to be restored to working condition. Moreover, additional sealing areas are often required, which must be considered potential sources of errors.

The aim of the flame atomization device based on the invention is therefore to improve a device such as initially described, in such a manner as to provide a simple construction for pressure release, or respectively, pressure reduction, and at the same time, to restore the flame atomization device to working condition simply and quickly.

This aim is achieved by mounting a slip casing that can be adjusted between a closed position and an open position in relation to the burner connection piece. At the same time, in the open position, at least one pressure reduction outlet is opened in the burner connection piece.

Because of the sliding of the slip casing, it is unnecessary to include a component that flies off, or a component that is to be destroyed by the pressure. This also obviates the need to mount a comparatively complex pressure relief valve. When a correspondingly high degree of overpressure builds up, the slip casing automatically slides into its open position, and the pressure is reduced through the burner connection piece's pressure reduction outlet. As a result, the pressure reduction outlet can be designed in such a way as to divert the escaping products without requiring additional, sensitive system parts. Likewise, such diversion may prevent injuries to personnel operating the device.

The slip casing may be located inside the burner connection piece in an adjustable manner. If the slip casing it is, for example, secured to the burner head in this position so that they move together, the slip casing may be slipped away together with the burner head when excess pressure occurs, and as a result, the pressure reduction outlet opens. Yet in order to configure the flame atomization device based on the invention in a simpler way and to avoid creating additional dead space inside the mixer chamber, which may lead to test delays between different samples, the slip casing can be mounted onto the burner connection piece from the outside. In this manner no modifications are required inside the burner connection piece.

The slip casing may also be configured as a partial covering; that is, the casing may only extend along a specific portion of the circumference around the burner connection piece. At the same time, the slip-casing may, as described above, be fixed to the burner head and, for example, be held in position by it, fitting tightly along one of the burner connection piece's outer walls. If in such a case, the burner head moves because of excess pressure inside the mixer chamber, the slip casing or partial casing will move accordingly, as well, and the pressure reduction outlet is opened. Yet in order to enable the slip casing to be mounted independently from the burner head or from other parts of the flame atomization device, the slip casing may possess a slip mantle that encloses the burner connection piece. In this manner, the slip casing itself may be attached to the burner connection piece so that it is movable.

In order to fasten the slip casing to the burner head in a way that it can move only between the closed and open positions and cannot detach from the burner head by itself, the slip casing may be fastened to the burner connection piece by a clip.

In order to limit the slip casing's freedom of movement between the closed and open positions, the slip casing may be mounted in a movable manner between the closed and open positions, yet at the same time be secured tightly onto the burning connection piece itself, in a way that prevents it from turning.

There are several ways to ensure such a type of mounting. A simple construction may include an essentially rib-like securing protrusion extending from the slip casing and/or the burner connection piece. This protrusion engages in a corresponding securing recess at the respective opposite part of the tightly secured, but axially movable bearing. In this manner, only one component is needed to ensure the mounting between the slip casing and the burner connection piece. At the same time, the closed and open positions may be determined by the sliding motion of the securing protrusion inside the securing recess. For example, the closed position may be determined by the securing protrusion's contact with one end of the arresting recess, and the open position may be accordingly defined by the securing protrusion's contact with the arresting depression's other end.

In order to prevent the slip casing from getting wedged during its axial movement, it could be of advantage to arrange two securing protrusions, and their corresponding arresting depressions, diametrically opposite each other.

Within this context, it has to be noted that it is, of course, possible to design a securing protrusion on the slip casing as well as on the burner connection piece. In this case, accordingly, there is one securing recess each on the slip casing or the burner connection piece. The securing protrusions and recesses of the different components are arranged in such a way, in relation to each other, that they engage each other as soon as the slip casing is in position. In addition, it must be noted that the slip casing may also be clipped onto the burner connection piece by means of the securing protrusion and the arresting depression. For example, the slip casing is clipped onto the burner connection piece when the securing protrusion engages in the arresting depression.

In order to create, in a simple manner, a certain pressure on the slip casing in order to move it into the open position, the slip casing may be engaged in a detachable way with the burner connection piece. In order to release the engagement, a certain force is required, which corresponds in its strength to a corresponding excess pressure inside the mixer chamber.

A simple implementation of such an engagement may be achieved by arranging a pin element on the slip casing and/or burner connection piece and on the respective opposite part an opposing slot element. It may be of advantage, too, to arrange the pin element and opposing slot element in pairs, diametrically opposing each other.

A simple realization of such an opposing pin and slot element combination may be achieved by designing the pin element as a widening and the opposing slot element as an essentially complementary recess. The widening may, for example be created on an inner side of the slip casing, and correspondingly, the recess may be created on one of the burner connection piece's outer sides. A reverse arrangement of pin and opposing slot element is possible, as well.

In order to allow a swift reduction of overpressure in the mixer chamber, even when the diameter of the pressure reduction outlet is small, a number (i.e. more than one) of pressure reduction outlets may be arranged in the burner connection piece, especially at an equal distance above the slip casing's bottom edge in its closed position. The pressure reduction outlets may be distributed unevenly so that preferably the fuel gas, or alternatively the burned produce, escapes at a certain angle. Preferably, the pressure reduction outlets are arranged at the burner connection piece's top end. Of course, it is equally possible to distribute the pressure reduction outlets unevenly, as far as their height is concerned, so that, for example, a pressure reduction occurs first from a smaller number of pressure reduction outlets, and in case of a higher excess pressure, finally, through all of the pressure reduction outlets. At the same time, corresponding pressure reduction outlets may be created, in addition, or even by themselves, in an area of the burner connection piece, an area which, when the slip casing is in open position, is open to the outside.

If, during a pressure build-up, there is no exertion of sensitive construction components in the mixer chamber's area, the pressure reduction outlets may also be arranged in pairs, opposite each other, or at an equal distance from each other along the circumference of the burner connection piece. This causes a pressure reduction essentially in all radial directions in relation to the burner connection piece.

In order to allow a simple reaction to excess pressure within the mixer chamber, the burner head may be fastened to the slip casing in a detachable manner. If there is excess pressure in the mixer chamber, it will affect the burner head and move it in relation to the burner connection piece, together with the slip casing. Thus the slip casing is moved from its closed position into its open position.

A simple detachable fastening of the burner head and the slip casing may be achieved if the burner head can be clipped to the slip casing at the slip casing's top end. This clipping connection must at least be sufficiently stable so that, when pressure is exerted on the burner head, the burner head does not detach from the slip casing and fly off uncontrollably, but instead moves the slip casing into its open position.

In order to be able to determine, preferably automatically, that there is overpressure inside the flame atomization device of this invention, which is reduced by moving the slip casing, the burner head's and/or the slip casing's movement may be recorded when the slip casing moves between its closed and open positions by means of a motion sensor device. If such a movement is registered, for example, a warning signal or something similar may be triggered.

A simple way to record such a position of the slip casing or the burner head is provided when the motion sensor device possesses at least one magnetic strip attached to the slip casing or the burner head, and a corresponding sensor. For example, the magnetic strip and the sensor may be arranged in relation to each other in such a way that the sensor reacts to the magnetic strip only when the slip casing is in its open position, thus triggering a warning signal.

In order to enable the burner head and slip casing to be fastened to each other in a simple way, a bayonet lock, especially one with two hooked noses shifted by 180°, may be arranged between the burner head and the slip casing.

In order to seal off the burner head and the slip casing from one other, and at the same time to ensure replacement of the burner head with little effort, a sealing element, especially an O-shaped ring, may be mounted between the burner head and the slip casing. If the pressure reduction outlets are located at the top end of the burner connection piece, the O-shaped ring seals the outlets against their surroundings when the slip casing is in closed position. At the same time, the O-shaped ring preferably is arranged below the pressure reduction outlets when in closed position. The pressure reduction outlets may be designed as slits or as fringe recesses opening toward the top edge of the burner connection piece.

In order to enable the burner head to be replaced or turned without problems, even when it is hot, the burner head may be equipped with a pivoted lever, which allows it to be fastened to and/or loosened from the slip casing. In such cases the pivoted lever is turned far enough to allow the bayonet lock between burner head and slip casing to be loosened, or alternatively to become engaged. Thereafter, the burner head may be removed or alternatively attached to the slip casing.

In order to mount the pivoted lever in a simple and swiveling manner, the pivoted lever may be equipped, at the end attached to the burner head, with a bearing section that is preferably circular in part. This section is fitted to the slip casing's outside and may be swiveled in relation to the case.

In order to configure the pivoted lever as a component independent from the burner head, the bearing section may be located and held between one of the slip casing's outer sides and one of the burner head's inner sides. If the burner head is loosened from the slip casing, the pivoted lever with its bearing section may be removed, too, from the slip casing in a simple manner.

In order to simplify the bearing section's arrangement between slip casing and burner head, the burner head's inside may consist of a burner apron, which at least partially encases the slip casing. For example, the burner apron may extend partially around the slip casing, analogous to the bearing section.

When the burner head is attached to the slip casing by clipping, the pivoted lever may be attached to the burner head in a simple manner, when the bearing section and the burner apron are arranged with respect to one another in a way the prevents them from turning. This may be achieved, for example, by the engagement of corresponding protrusions and recesses in the area of the bearing section and burner apron.

In order to prevent, especially automatically, any additional damage to the flame atomization device from excess pressure, it may be possible to have the flame shut off at least when the motion sensor device registers the open position. This may be achieved, for example, by interrupting an electronically controlled fuel gas influx into the mixer chamber.

In order to be able to determine, in addition, whether the burner head is properly mounted onto the slip casing, the motion sensor device may be equipped with a detector, which registers either an angle position between burner head and slip casing and/or a type of burner head. This detector, too, may be composed of at least one magnetic strip and a matching sensor. It may be determined that the burner head is fastened properly to the slip casing, for example, by registering the magnetic strip on the slip casing only in such a pivoting range in which a proper fastening of the burner head on the burner connection piece is guaranteed. The bayonet lock is found between the burner head and the slip casing, when the slip casing is in closed position, only within this pivoting range.

Finally, the detector may also be used to register a type of burner head. In this case, for example, depending on the type of burner head, at least one corresponding magnetic strip changes its position at the burner head. At the same time, the magnetic strips may be designed separately in order to register the type of burner head and the angled position between the burner head and the slip casing.

BRIEF DESCRIPTION OF DRAWINGS

Hereafter an advantageous embodiment of the invention is further explained by means of the illustrations. The illustrations are as follows.

DETAILED DESCRIPTION OF DRAWINGS

Figure 1:
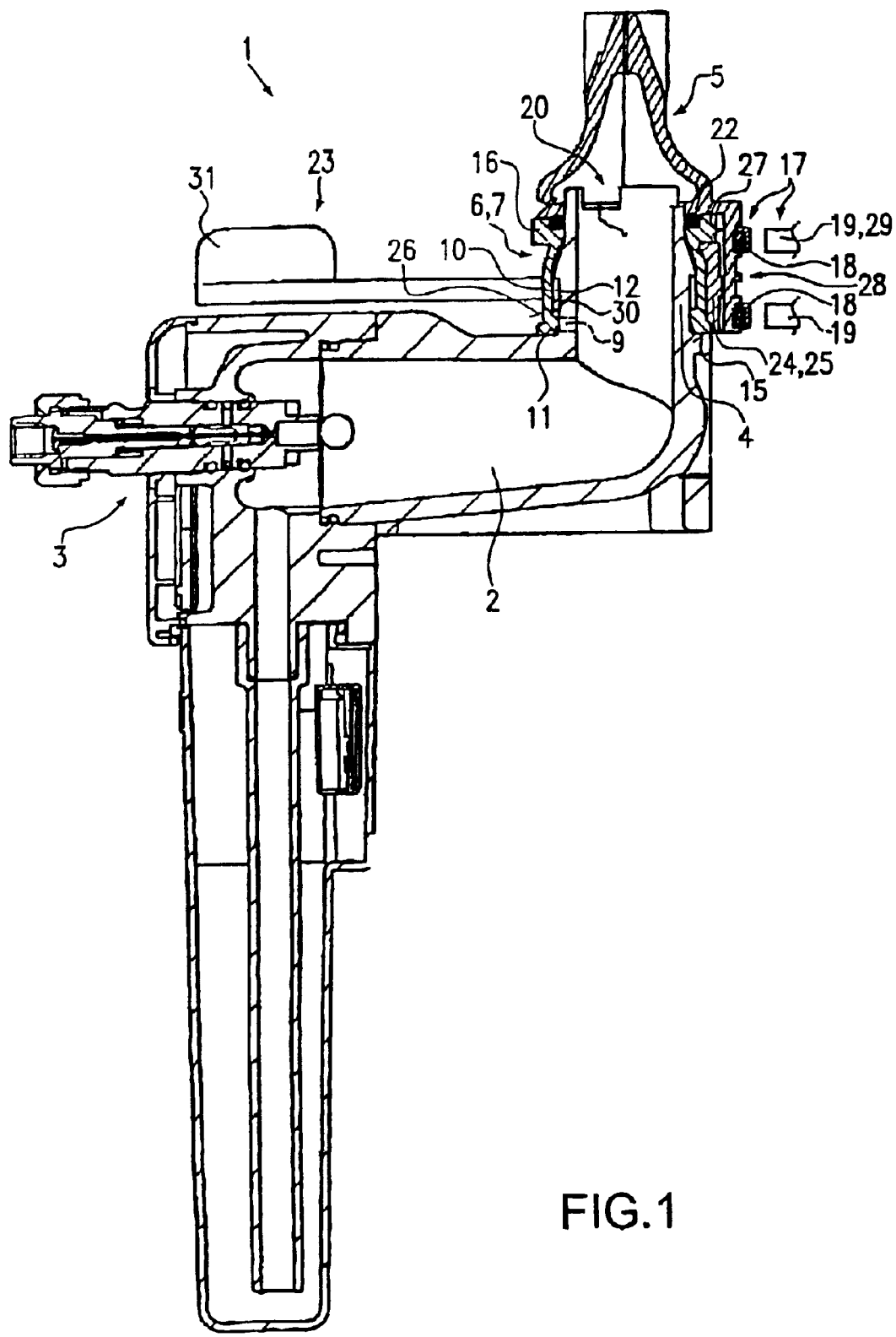
FIG. 1 Vertical section through a sample design of the flame atomization device based on the invention.

FIG. 1 shows a vertical section through a sample design of a flame atomization device 1 based on the invention. This version is equipped with an atomizer 3 on its side, which leads into a mixer chamber 2. The mixer chamber 2 possesses a burner connection piece 4, which runs upward in FIG. 1, and onto which a burner head 5 is mounted.

A slip casing 6 in its closed position 7 is clipped onto the outside surface of the burner connection piece 4. On the inside 30 next to the lower edge 15, the slip casing 5 includes a rib-shaped securing protrusion 11, which extends in axial direction. This protrusion is inserted into a groove-like securing recess 12 and can be moved along this recess, between the closed position 7 and the open position 8, as in FIG. 2. The slip casing 6 is clipped onto the burner connection piece 4 when the securing protrusion 11 engages in the securing recess 12.

The securing protrusion 11 and the securing recess 12 are arranged in pairs opposite each other.

An upper end 16 of the slip casing 6 is equipped with a flange extending outward in radial direction. The burner head 5 is clipped to the upper end 16. It is equipped with a burner apron 28, which is approximately partly circular in its cross-section, and which is clipped to the slip casing 6 from the outside. Between the upper end 16 of the slip casing 6 and the burner head 5, an O-shaped ring 22 is mounted, which serves as a sealing element between the two components.

One of the outer sides of the burner apron 28 has at least two magnetic strips 18, arranged at a distance to each other and running in axial direction. The lower magnetic strip 18 seen in FIG. 1 serves to register the closed position 7 of the slip casing 6. The magnetic strips 18 are part of a motion sensor device 17. Each magnetic strip 18 is assigned a sensor 19. The sensor 19 assigned to the upper magnetic strip 18 in FIG. 1 serves as a detector 29, which serves to register an angular area and/or to identify the type of burner head. On the one hand, this sensor makes it possible to determine whether the burner head 5 is located in such an angular area, in which the bayonet lock 10 between the burner head 5 and the slip casing 6 is safely locked—relative to the slip casing 6, which is movable in axial direction yet attached to the burner connection piece in a way that prevents it from turning. On the other hand, the same magnetic strip or an additional magnetic strip may determine whether a specific type of burner head has been installed.

Figure 2:
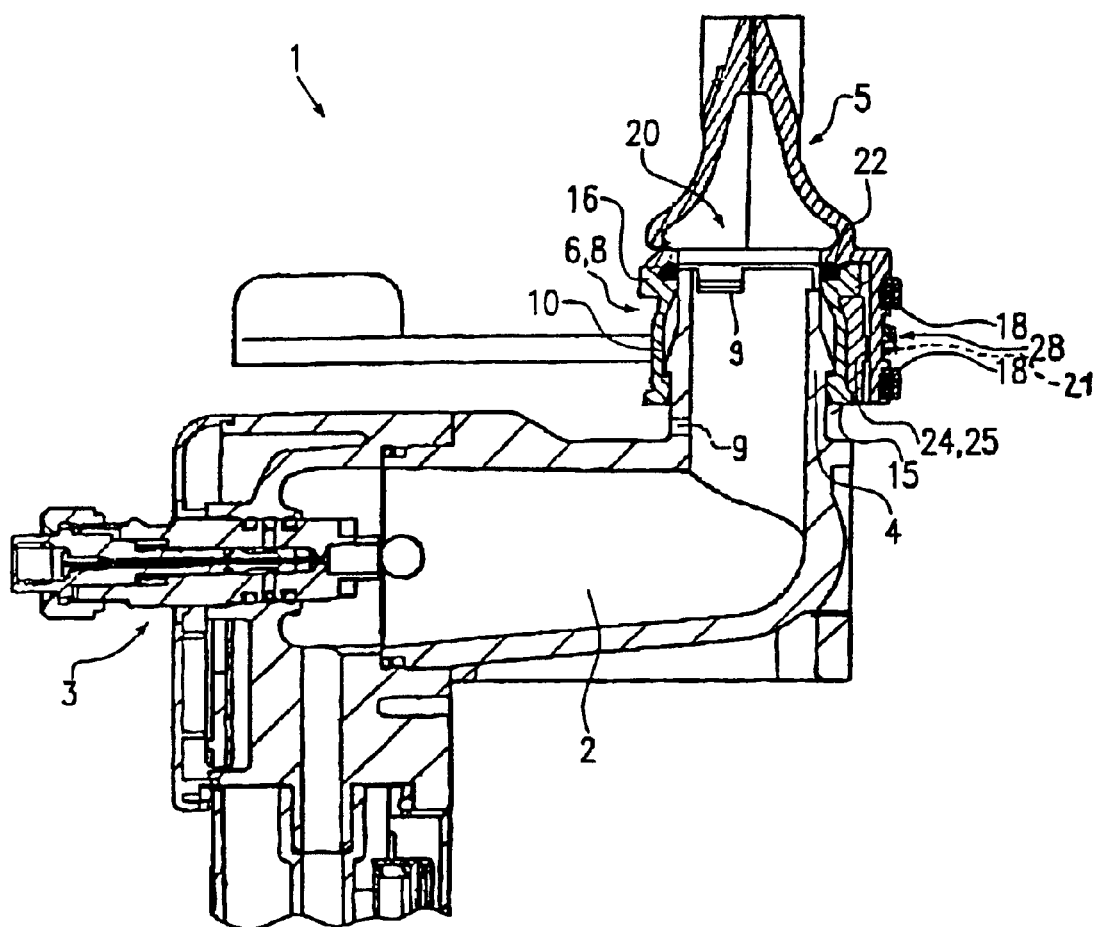
FIG. 2 Vertical section similar to FIG. 1, including the slip casing in open position.

Different types of burner head can be registered by different axial positions of the corresponding magnetic strips. For example, the positioning of the two magnetic strips according to FIGS. 1 and 2 corresponds to a first type of burner head, while for a second type of burner head the upper magnetic strip according to FIGS. 1 and 2, is arranged in axial direction and shifted downward—see reference 21. The two types of burner head may, for example, have different slit lengths.

The burner head 5 may be swiveled in relation to the slip casing 6 by means of a pivoted lever 23. The pivoted lever is equipped with a working end 31. At the end 24 opposite its working end 31, the pivoted lever 23 possesses a bearing section 25, whose cross-section is circular. This bearing section is located between an outer side 26 of the slip casing 6 and an inner side 27 of the burner head 5, as in FIG. 2. The bearing section 25 is connected to the burner apron 28 in a way that prevents it from turning so that a swiveling motion of the pivoted lever 23 around the slip casing 6 results in a corresponding swiveling motion of the burner head 5 in relation to the slip casing 6. In this manner, the burner head may both be detached from and fastened to the slip casing 6.

The slip axial mobility of the slip casing 6 in relation to the burner connection piece 4 is made possible by the engagement of the securing protrusion 11 and the securing recess 12. Since the securing protrusion 11 is rib-shaped and the securing recess 12 is groove-like, their mutual engagement, in addition, keeps the slip casing 6 from turning in relation to the burner connection piece 4.

FIG. 2 show a section analogous to FIG. 1, with the slip casing 6 seen in its open position 8. The same parts are assigned the same numbers in all figures, although at times only certain parts are explicitly mentioned in the context of a figure.

The open position 8 is determined when the securing protrusion 11 contacts the upper end of the arresting device 12 according to FIG. 2. In FIG. 2, the burner head 5 has moved upward, together with the slip casing 6. In the open position 8, the pressure reduction outlets 9 are open—only one of them is shown in FIGS. 1 and 2. The pressure reduction outlets 9 are dispersed on the burner connection piece 4 so that, in case of overpressure, fuel gas or corresponding combustion products may escape from the mixer chamber 2 to the outside. The respective excess pressure in the mixer chamber 2 pushes the burner head 5 upward, and through its connection to the slip casing 6, the burner head 5 pushes the case upward into its open position 8. In the closed position 7 of the slip casing 6, as in FIG. 1, the O-shaped ring 22 is located below the pressure reduction outlets 9 so that the outlets are sealed off from the outside. The pressure reduction outlets 9 are preferably designed as slits and located next to the upper end of the burner connection piece 4. In addition to, or instead of, the pressure reduction outlets 9, the pressure reduction outlet 9 indicated by the dotted line may be arranged at the lower end of the burner connection piece 4.

The sliding motion into the open position 8 may be registered by the motion sensor device 17, as in FIG. 1. If the open position 8 is accordingly registered, the flames are extinguished by a corresponding signal emitted by the motion sensor device 17.

After the flames are extinguished and the overpressure relieved, the burner head 5 and the slip casing 6 may be moved back again downward, as seen in FIG. 2, until the slip casing 6 returns to its closed position 7, as in FIG. 1. Subsequently, the flame atomization device based on the invention is operational again.

Figure 3:
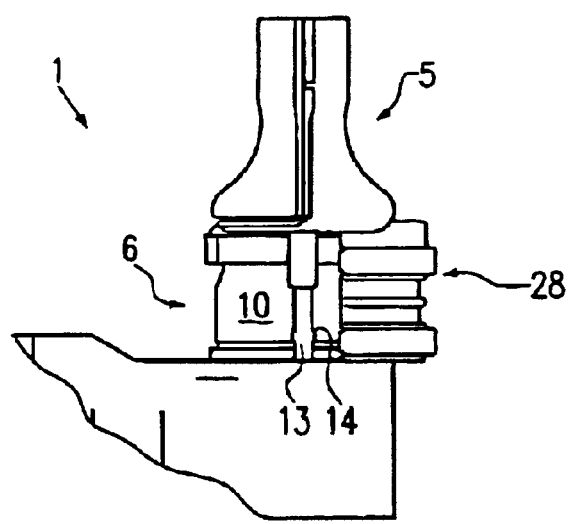
FIG. 3 Lateral view of the burner head and the slip casing of the flame atomization device based on the invention.

FIG. 3 shows a side view of the flame atomization device 1, especially of the area of the burner head 5 and the slip casing 6. In addition to the previous description, it can be seen that the slip casing 6 in its closed position 7 can be engaged, or secured. The engagement, or securing, is achieved by a widening serving as pin element 13, which engages in a corresponding recess serving as the opposite slot element 14 in the closed position 7. The engagement is defined in a way that requires a certain overpressure within the mixer chamber 2 and a corresponding thrusting force upward—as in FIGS. 1 and 2—before the slip casing leaves its engagement in its closed position 7 in the direction of its open position 8.

If the burner head 5 is detached from the slip casing 6 by a swiveling motion of the pivoted lever, it may be removed upward in axial direction. Subsequently, the pivoted lever 23 may be detached from the slip casing as well, with the bearing section 25 moving essentially outside in radial direction, away from the slip casing 6. After that, if necessary, the slip casing 6 may also be removed from the burner connection piece 4.

The invention offers a simple option for pressure reduction in case of excess pressure inside the mixer chamber. At the same time, the burner head is easily attached and removed. The slip casing mounted outside does not require additional sealing and, in its open position, guarantees fast and sufficient pressure reduction via the corresponding pressure reduction outlets 9. At the same time, the motion sensor device 17 may register that such a pressure reduction is taking place so that the flames may be extinguished automatically. Through the use of the bayonet lock and axial sealing by means of a sealing element 22, the burner head is easily turned and replaced, minimizing the required manual effort.

Following pressure reduction, the flame atomization device based on the invention may be easily returned to its operating condition by pressing the slip casing 6 down and back again into its closed position 7.

What is claimed is:

1. Flame atomization device, especially for an atom absorption spectrometer, with at least one mixer chamber and an atomizer leading into said mixer chamber, and with a burner head mounted on the mixer chamber's burner connection piece, characterized in that a slip casing is mounted so that it can slide between a closed position and an open position in relation to the burner connection piece while, in the open position, at least one pressure reduction outlet is opened in the burner connection piece.

2. Flame atomization device in accordance with claim 1, characterized in that the slip casing is mounted from outside on the burner connection piece.

3. Flame atomization device in accordance with claim 1, characterized in that the slip casing has a slip mantle that encloses the burner connection piece.

4. Flame atomization device in accordance with claim 3, characterized in that the slip casing is clipped onto the burner connection piece.

5. Flame atomization device in accordance with claim 4, characterized in that the slip casing is movable in axial direction yet attached to the burner connection piece in a way that prevents it from turning.

6. Flame atomization device in accordance with claim 5, characterized in that an essentially rib-like securing protrusion extends from the slip casing and/or the burner connection piece and this protrusion engages in a corresponding securing recess at the respective opposite part of the non-turnable placement.

7. Flame atomization device in accordance with claim 6, characterized in that two securing protrusions and securing recesses are installed diametrically opposite one another.

8. Flame atomization device in accordance with claim 7, characterized in that the slip casing in its closed position is detachably engaged with the burner connection piece.

9. Flame atomization device in accordance with claim 8, characterized in that a pin element is installed on the slip casing and/or burner connection piece and an opposing slot element is mounted on the respective opposite part.

10. Flame atomization device in accordance with claim 9, characterized in that the pin element is configured as a widening and the opposing slot element as an essentially complementary recess.

11. Flame atomization device in accordance with claim 10, characterized in that a number of pressure reduction outlets are arranged in the burner connection piece.

12. Flame atomization device in accordance with claim 11, characterized in that the pressure reduction outlets are arranged at an equal distance from each other along the circumference of the burner connection piece.

13. Flame atomization device in accordance with claim 12, characterized in that the burner connection piece is secured to but removable from the slip casing.

14. Flame atomization device in accordance with claim 13, characterized in that the burner head can be clipped to the slip casing at the top end of said slip casing.

15. Flame atomization device in accordance with claim 14, characterized in that a movement of the burner head and/or of the slip casing is recorded when the slip casing moves between its closed and open positions by means of a motion sensor device.

16. Flame atomization device in accordance with claim 15, characterized in that the motion sensor device possesses at least one magnetic strip attached to the slip casing or the burner head, and a corresponding sensor.

17. Flame atomization device in accordance with claim 16, characterized in that a bayonet lock is arranged between the burner head and the slip casing.

18. Flame atomization device in accordance with claim 17, characterized in that a sealing element is mounted between the burner head and the slip casing, and that the pressure reduction opening is installed in the closed position of the slip casing above the sealing element.

19. Flame atomization device in accordance with claim 18, characterized in that the burner head is equipped with a pivoted lever, which allows it to be fastened to and/or loosened from the slip casing.

20. Flame atomization device in accordance with claim 19, characterized in that the pivoted lever on its end facing the burner head has a bearing section that is circular in part that is fitted to the outside of the slip casing and is swiveled in relation to the casing.

21. Flame atomization device in accordance with claim 20, characterized in that the bearing section is mounted between the outside of the slip casing and an inner side of the burner head.

22. Flame atomization device in accordance with claim 21, characterized in that the inner side of the burner head is formed by a burner apron that at least partly surrounds the slip casing.

23. Flame atomization device in accordance with claim 22, characterized in that, when the burner is clipped onto the slip casing, the bearing section and the burner apron are arranged with respect to one another in a way the prevents them from turning.

24. Flame atomization device in accordance with claim 23, characterized in that, at least when the open position is registered by the motion sensor device, the flame can be extinguished.

25. Flame atomization device in accordance with claim 24, characterized in that the motion sensor device has at least one additional detector for registering an angled position between the burner head and the slip casing and/or a type of burner head.

* * * * *